(12) United States Patent
Pather et al.

(10) Patent No.: US 12,268,425 B2
(45) Date of Patent: *Apr. 8, 2025

(54) ORTHOPAEDIC BONE STABILISATION DEVICE

(71) Applicant: FIELD ORTHOPAEDICS PTY LTD, Red Hill (AU)

(72) Inventors: Shanthan Pather, Red Hill (AU); Jarred Bairstow, Red Hill (AU)

(73) Assignee: FIELD ORTHOPAEDICS PTY LTD, Red Hill Qld (AU)

( * ) Notice: Subject to any disclaimer, the term of this patent is extended or adjusted under 35 U.S.C. 154(b) by 0 days.

This patent is subject to a terminal disclaimer.

(21) Appl. No.: 18/523,292

(22) Filed: Nov. 29, 2023

(65) Prior Publication Data

US 2024/0090930 A1    Mar. 21, 2024

Related U.S. Application Data

(63) Continuation of application No. 17/117,826, filed on Dec. 10, 2020, now Pat. No. 11,857,234.

(30) Foreign Application Priority Data

Apr. 16, 2020  (AU) .................................. 2020901202

(51) Int. Cl.
*A61B 17/86* (2006.01)
*A61B 17/88* (2006.01)

(52) U.S. Cl.
CPC ........ *A61B 17/863* (2013.01); *A61B 17/8615* (2013.01); *A61B 17/8897* (2013.01)

(58) Field of Classification Search
CPC .... A61B 17/86; A61B 17/8625; A61B 17/863
See application file for complete search history.

(56) References Cited

U.S. PATENT DOCUMENTS

| | | | |
|---|---|---|---|
| 11,147,604 B2 | 10/2021 | Champagne et al. | |
| 2008/0234763 A1* | 9/2008 | Patterson | A61B 17/863 |
| | | | 606/301 |

(Continued)

FOREIGN PATENT DOCUMENTS

| | | |
|---|---|---|
| EP | 2613721 A1 | 7/2013 |
| EP | 3137645 A1 | 3/2017 |

(Continued)

OTHER PUBLICATIONS

India Office Action issued Feb. 8, 2022 re: Application No. 202144017779, pp. 1-6, citing: EP2613721A4, EP3137645A4 and EP3300676A1.

*Primary Examiner* — Si Ming Ku
(74) *Attorney, Agent, or Firm* — CANTOR COLBURN LLP

(57) ABSTRACT

An orthopaedic bone stabilisation device includes an elongate and integrally formed body having a length extending between proximal and distal ends. The elongate body includes a first threaded section having a head at the proximal end, the head configured to interface with a driver, the threaded section having external threads extending along a length of the first threaded section. The first threaded section extends between the proximal end and a first location of the elongate body. The first threaded section tapers from the proximal end to the first location such that the outer thread diameter of the first section gradually decreases from the proximal end to the first location of the elongate body. The device further includes a second threaded section having external threads, a length, and a substantially uniform thread diameter, and extends between the distal end of the elongate body and a second location of the elongate body.

17 Claims, 6 Drawing Sheets

(56) References Cited

U.S. PATENT DOCUMENTS

| | | | |
|---|---|---|---|
| 2015/0150613 A1* | 6/2015 | Gauneau | A61B 17/8625 606/315 |
| 2016/0015438 A1 | 1/2016 | Elleby et al. | |
| 2018/0235681 A1 | 8/2018 | Chambers et al. | |
| 2021/0153911 A1 | 5/2021 | Stuart et al. | |
| 2021/0353337 A1 | 11/2021 | Kaufmann et al. | |
| 2021/0369314 A1 | 12/2021 | Preiss-Bloom et al. | |
| 2022/0175434 A1 | 6/2022 | Champagne et al. | |

FOREIGN PATENT DOCUMENTS

| | | |
|---|---|---|
| EP | 3300676 A1 | 4/2018 |
| WO | 2012064401 A1 | 5/2012 |
| WO | 2015168311 A1 | 11/2015 |

* cited by examiner

ORTHOPAEDIC BONE STABILISATION DEVICE

CROSS-REFERENCE TO RELATED APPLICATIONS

This application is a continuation application of U.S. patent application Ser. No. 17/117,826, filed on Dec. 10, 2020, which itself claims the benefit of Australian Application No. 2020901202, filed on Apr. 16, 2020, all of which said applications are hereby incorporated by reference in their entirety.

TECHNICAL FIELD

The present disclosure relates to an orthopaedic bone stabilisation device that is implantable in a bone to stabilize the bone while the bone heals, and which is particularly but not exclusively suitable for use in stabilisation and healing of a metacarpal bone.

BACKGROUND

Any references to methods, apparatus or documents of the prior art are not to be taken as constituting any evidence or admission that they formed, or form part of the common general knowledge.

Fractures of small long bones, such as but not limited to metacarpal, metatarsal bones, clavicle, ulna, radius and fibula, are common and the size and location of these bones make traditional healing methods complex. Newer less invasive techniques include boring of the metacarpal bone followed by inserting a pin or a K-wire in order to fasten bone fractures. Fracture fixation methods for phalangeal, metacarpal, and metatarsal bones rely upon the use of Kirschner wires (K-wires) to stabilize the bone at the line of fracture. K-wires are usually left proud above the bone and do not have a fixation point per se. The K-wires are left proud so that they can be removed at a later date. However, when K-wires are left proud, the region around the inserted K-wire is prone to becoming infected. Because of their lack of point fixation, the K-wire can also end up migrating or loosening. This results then in potential loss of the fixation with either malunion or non-union. There has also been a rise in the use of fixating bolts, pins with or without combination with plates. However, such methods have their own shortcomings. Specifically, conventional screws do not have a suitable shape especially for intramedullary placement. Further, such screws or nails may not achieve the desired level of fixation. In view of the above, it is desirable to provide an improved bone stabilisation device which addresses some of the problems of the prior art.

SUMMARY

In an aspect, the disclosure provides an orthopaedic bone stabilisation device comprising: an elongate and integrally formed body having a length (L) extending between a proximal end and a distal end with a cannula extending therethrough, the elongate body further comprising: a first threaded section comprising a head located at the proximal end, the head being configured to interface with a driver, the threaded section comprising external threads extending along a length (L1) of the first threaded section, the first threaded section extending between the proximal end of the elongate body and a first location of the elongate body wherein the first threaded section tapers from the proximal end to the first location such that outer thread diameter ($D_T1$) of the first section gradually decreases from the proximal end to the first location of the elongate body, and a second threaded section comprising external threads, the second threaded section having a length (L2) and a substantially uniform thread diameter ($D_T2$) and extending between the distal end of the elongate body and a second location of the elongate body.

In an embodiment, the orthopaedic bone stabilisation device further comprises: a non-threaded section having a length (L3) positioned between the first and second threaded sections wherein said non-threaded section extends between the first and second locations of the elongate body.

In an embodiment, the non-threaded section comprises a uniform diameter along the length L3 of the non-threaded section.

In an embodiment, the length (L3) of the non-threaded section is less than 50% of the length of the elongate body.

In an embodiment, each of the first and second threaded sections comprises a respective shank diameter denoted by D1 and D2 respectively which denote the diameter of the unthreaded portions of the shank in each of the first and second sections of the elongate body. Consequently, D1 may also gradually decrease from the proximal end to the first location of the elongate body.

In an embodiment, shank diameter (D3) of the non-threaded section is substantially equal to shank diameter (D2) of the second section.

In an embodiment, the outer thread diameter ($D_T1$) of the first section at the proximal end is 1.2 to 1.6 times the outer diameter ($D_T1$) of the first section at the first location. Similarly, the shank diameter (D1) of the first section at the proximal end is 1.2 to 1.6 times the outer diameter (D1) of the first section at the first location.

In an embodiment, the outer thread diameter ($D_T1$) of the first section at the proximal end is 1.3 to 1.5 times the outer thread diameter ($D_T1$) of the first section at the first intermediate end. Similarly, the shank diameter (D1) of the first section at the proximal end is 1.3 to 1.5 times the outer diameter (D1) of the first section at the first location.

In an embodiment, length (L1) of the first section is in the range of 0.2 L and 0.5 L.

In an embodiment, length (L1) of the first section is at least 0.25 L.

In an embodiment, length (L2) of the second section is in the range of 0.2 L and 0.5 L.

In an embodiment, length (L2) of the second section is at least 0.25 L.

In an embodiment, the threads on the first section have the same pitch as the pitch of the threads on the second section.

In an embodiment, at least one of said first or second sections further comprises one or more cutting flutes.

In an embodiment, the cutting flutes are located at circumferentially spaced positioned along the first and/or second threaded sections and interrupting the threads.

In an embodiment, the cutting flutes are helical flutes that extend continuously along the first and/or second threaded sections.

In another aspect, the disclosure provides a method of repairing a bone utilizing an orthopaedic bone stabilisation device, the device comprising: an elongate and integrally formed body having a length (L) extending between a proximal end and a distal end with a cannula extending therethrough, the elongate body further comprising: a first threaded section comprising a head located at the proximal end, the head being configured to interface with a driver, the threaded section comprising external threads extending along a length (L1) of the first threaded section, the first threaded section extending between the proximal end of the elongate body and a first location of the elongate body wherein the first threaded section tapers from the proximal end to the first location such that outer diameter (D1) of the first section gradually decreases from the proximal end to the first location of the elongate body, and a second threaded section comprising external threads, the second threaded section having a length (L2) and a substantially uniform diameter (D2) and extending between the distal end of the elongate body and a second location of the elongate body, the method comprising the steps of:

(a) inserting a guide wire into a fractured bone to extend the guide wire across one or more fractures in the bone;

(b) positioning the entire length (L) of the bone stabilisation device completely into the bone by (i) positioning the guide wire in the cannula of the stabilisation device, (ii) rotationally driving the device by engaging a driving end of a driving tool with the head of the device and rotatably driving the device using the driving tool over the guide wire, until the device is positioned completely inside the opening on each side of the fracture in order to stabilize the bone.

BRIEF DESCRIPTION OF THE DRAWINGS

Preferred features, embodiments and variations of the disclosure may be discerned from the following Detailed Description which provides sufficient information for those skilled in the art to perform the disclosure. The Detailed Description is not to be regarded as limiting the scope of the preceding Summary of the Disclosure in any way. The Detailed Description will make reference to a number of drawings as follows.

DETAILED DESCRIPTION OF THE DRAWINGS

Figure 1:
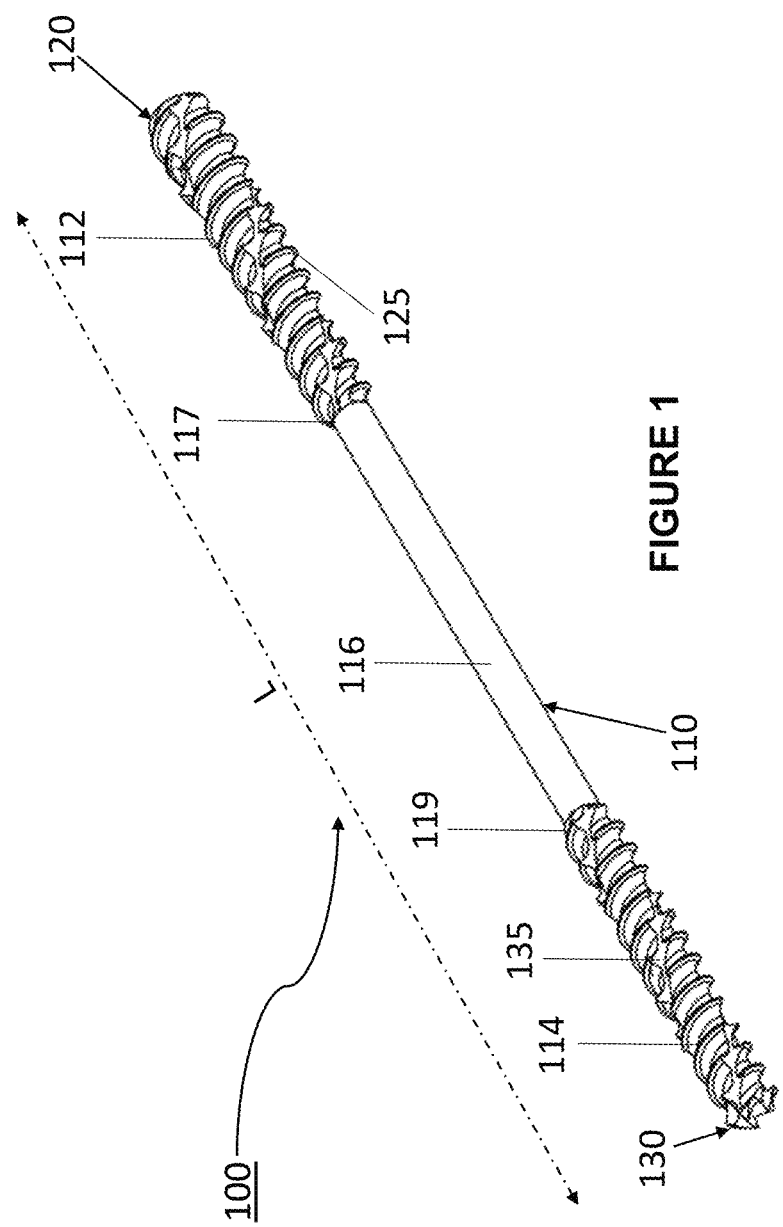
FIG. 1 is a right hand side perspective view of a bone stabilisation device 100 in accordance with a first embodiment.
Figure 2:
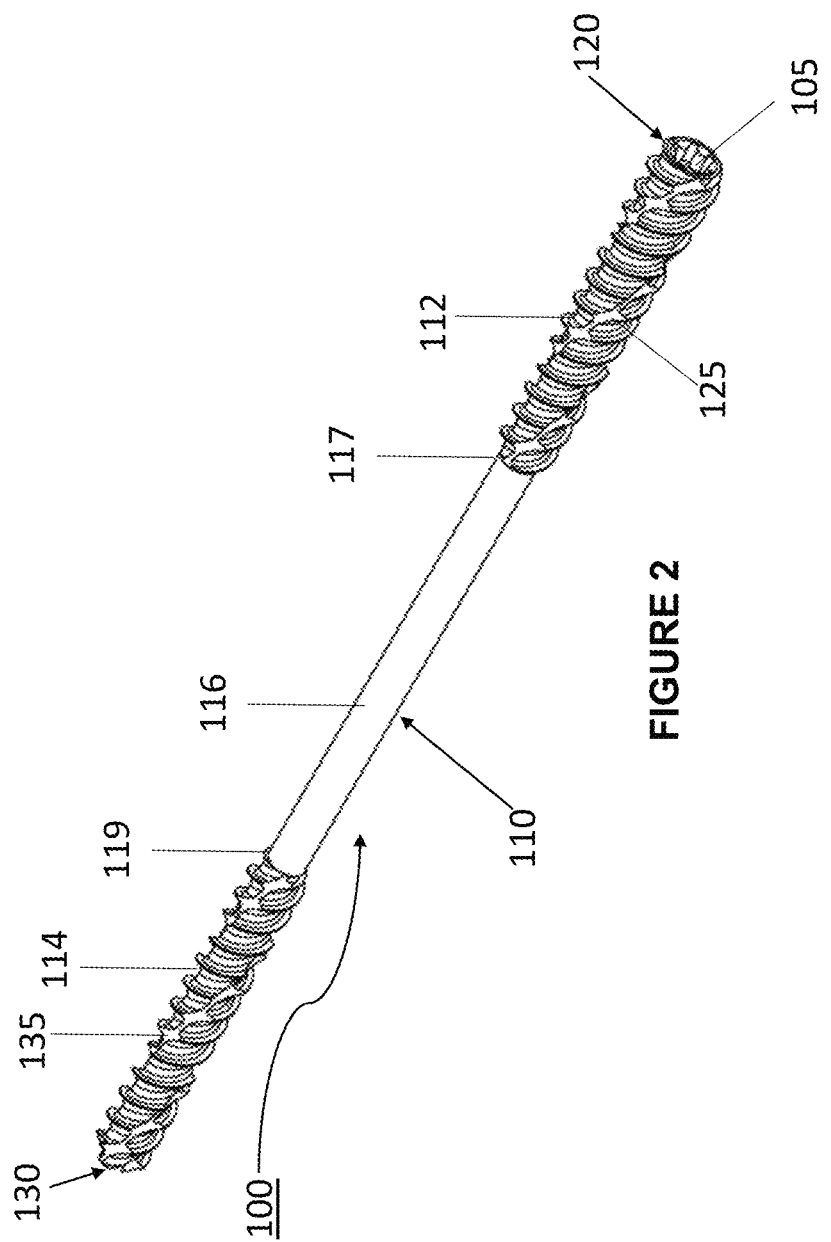
FIG. 2 is a left hand side perspective view the bone stabilisation device 100.

Throughout this disclosure mention is made of several terms which are defined herein as follows: (a) the term "lead" refers to the measurement of the distance along the screw's longitudinal axis that the screw advances relative to a fixed point upon exercising one complete revolution of the screw about its longitudinal axis; (b) the term "pitch" refers to the distance between adjacent thread crests on a screw; (c) the term "single thread" is used to denote a screw or a screw portion having a single continuous helical thread, with a single thread start, on the screw or screw portion; (d) the term "double thread" is used to denote a screw or a screw portion having two continuous helical threads, with two separate thread starts, on the screw or screw portion.

It should be noted that in the prior art it is common, albeit technically incorrect, to use the terms "lead" and "pitch" interchangeably. This is so because the pitch and lead of a screw having a single thread (which a common configuration) is identical. However the same is not the case for screws having multiple threads, such as double threads. Accordingly, the present disclosure references relative pitches between portions of screws having only single threads. For screws having one or more portions with a multiple thread, lead is referenced.

FIGS. 1 to 5 illustrate an exemplary embodiment of an orthopaedic bone stabilisation device 100 which is particularly suitable for stabilisation and healing of metacarpal bones. The stabilisation device 100 comprises an elongate body 110 having a length (L) which may range from 20 mm to 90 mm that may be made from any suitable material including but not limited to surgical grade stainless steel, Titanium and Titanium alloys. In the presently described embodiment, the elongate body 110 is shown to be cannulated with the cannula 105 extending through the entire elongate body 110 between a proximal end 120 and a distal end 130. As a result, the elongate body comprises an inner diameter ($D_C$) and an outer diameter (D) which will be discussed in further detail throughout the specification. Any references to the term "diameter" hereinafter effectively refer to the outer diameter. In other alternative embodiments, the elongate body 110 may not have a cannula and in such embodiments the stabilisation screw 100 may have a slightly reduced diameter without departing from the spirit and scope of the disclosure.

Figure 3:
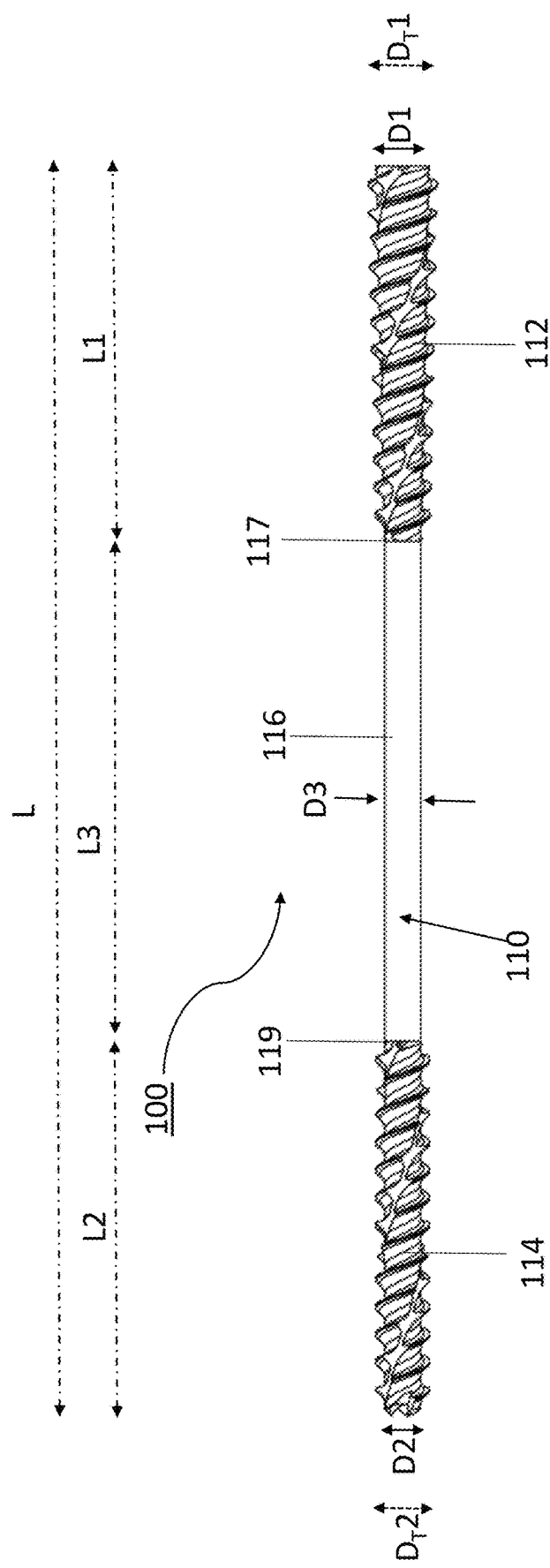
FIG. 3 is a side view of the bone stabilisation device 100.
Figure 5:
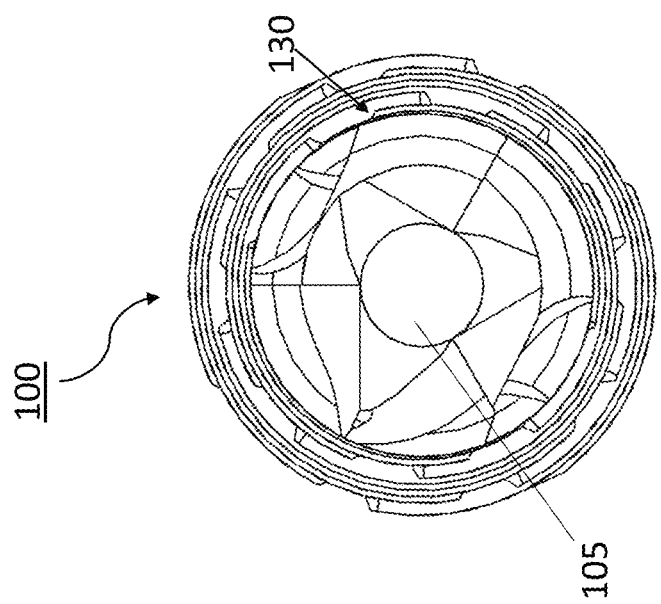
FIG. 5 is an end view of the distal end 130 of the bone stabilisation device 100.
Figure 4:
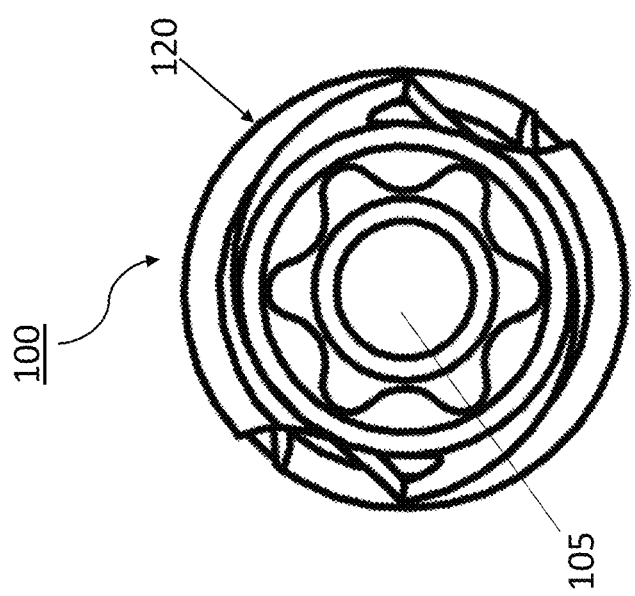
FIG. 4 is an end view for the proximal end 120 of the bone stabilisation device 100.

The elongate body 110 comprises a first threaded section 112, a second threaded section 114. The first threaded section 112 includes a head 122 located at the proximal end 120 that is adapted to interface with a driver. The head 122 may be configured to interface with any suitable driver configuration including but not limited to a torx-drive, hex head or any other suitable configuration. The first threaded section 112 has a length (L1) whereby L1 is preferably 0.3 to 0.5 times the length (L) of the elongate body 110. Referring to FIG. 3 in particular, the first threaded section 112 extends from the proximal end 120 to a first location 117 of the elongate body 110 such that the outer thread diameter ($D_T 1$) of the first section 112 gradually decreases from the proximal end 120 to the first location 117 of the elongate body 110. In the preferred embodiment, the outer thread diameter ($D_T 1$) decreases uniformly in a direction from the proximal end 120 towards the first location 117 to provide a substantially tapered configuration for the first threaded section 112. In other embodiments, the outer thread diameter $D_T 1$ may decrease in a non-uniform manner without departing from the disclosure. Preferably, the outer thread diameter ($D_T 1$) of the first section at the proximal end is 1.2 to 1.6 times the outer diameter ($D_T 1$) of the first section 112 at the first location 117 resulting in the tapered configuration of the first threaded section 112. The first threaded section 112 has a shank diameter denoted generally by D1. The shank diameter D1 of the first section 112 also progressively decreases uniformly from the proximal end 120 towards the first location 117 and the shank diameter (D1) of the first section at the proximal end is 1.2 to 1.6 times the shank diameter (D1) of the first section 112 at the first location 117. The importance of the configuration for the first threaded section 112 will be explained in detail in the foregoing sections.

The second threaded section 114 has a length (L2) which extends between the distal end 130 and a second intermediate location 119 on the elongate body 110. L2 is preferably 0.3 to 0.5 times the length (L) of the elongate body 110. The entire length of the second section 114 comprises helical threads. The second section 114 also has an outer thread diameter ($D_T2$) and shank diameter (D2) and preferably these diameters are substantially equal to the outer thread diameter ($D_T1$) and shank diameter (D1) respectively at the first location 117.

In some embodiments, the stabilisation device 100 may only comprise the first and second threaded sections 112 and 114 in which case the first location 117 and the second location 119 on the elongate body 110 may lie on the same point. However, in the presently described embodiment, the stabilisation device 100 further includes a non-threaded section 116 that is positioned between the first and second threaded sections 112 and 114. The non-threaded section 116 does not have any helical threads thereon and has a length (L3) that lies between the first location 117 and the second location 119. The length (L3) of the non-threaded section is preferably less than 0.5 times the length (L) of the entire elongate body 110. Preferably, outer shank (D3) of the non-threaded section 116 is substantially equal to the shank diameter (D2) of the second section 114. Once again, the importance of the configuration for the non-threaded section 116 will also be explained in detail in the foregoing sections.

Advantageously, each of the first and second threaded sections 112 and 114 include cutting structures in the form of continuous helical flutes 135 that interrupt the helical threads of the first and second sections 112 and 114.

Figure 6:
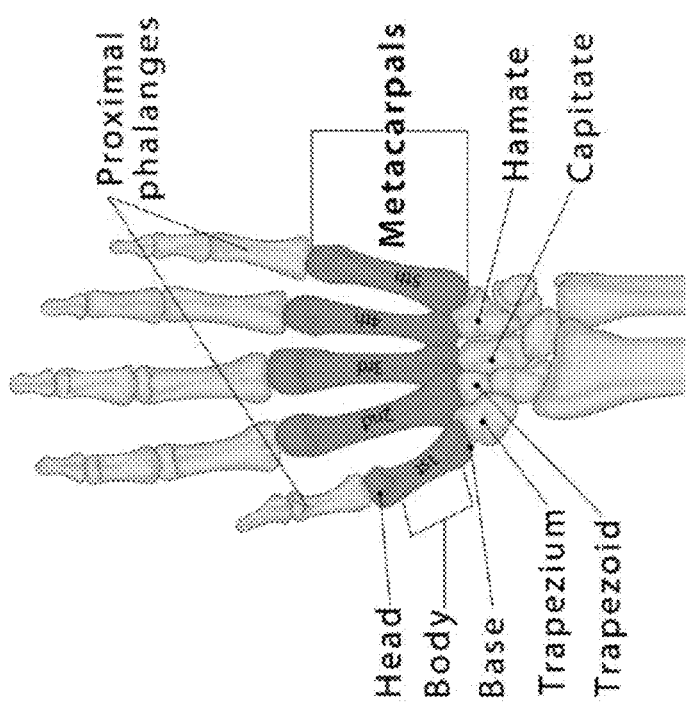
FIG. 6 is a plan view of the skeletal system for a human hand.

In at least one form, the stabilisation device 100 may be used for supporting or stabilisation of a damaged metacarpal bone during healing. FIG. 6 shows the skeletal system of a human hand with the metacarpal bones being highlighted. A method of installing the stabilisation device 100 may involve aligning the damaged metacarpal bone into an aligned position followed by insertion of a pin or a K-wire into the damaged metacarpal bone through the base portion of the metacarpal bone. As discussed above, insertion of the K-wire into a damaged bone is known. It would be understood by a skilled person that a K-wire with the appropriate size should be used depending on the physiological characteristics of the bone being repaired. For example, K-wires may be available in range of diameters from 0.8 mm to 1.6 mm.

Once the K-wire has been inserted, the next step involves the use of a cannulated drill that uses the K-wire as a guiding means to drill a bore into the damaged bone. Preferably, the diameter of the cannulated drill bit being used to create the bore may be suitably sized to allow the diameter of the stabilisation device 100 to be accommodated within the bone. Once the bore has been suitably drilled into the damaged bone, a driver with a suitable interface is used to rotate and drive the stabilisation device 100 into the bore. As has been previously explained, the head 122 interfaces with the driver and the distal end 130 of the stabilisation device 100 is initially driven into the head portion/section (the first section) of the drilled bore of the damaged bone (requiring stabilisation). The second section 114 includes double threads that are intertwined and run parallel to each other. The provision of the double threads allows the lead distance of a thread to be increased without changing the pitch of the thread. For example, the double start thread for the second section 114 has double the lead distance when compared to a single start thread having the same pitch. Another design advantage of a multi-start thread provided on the second section 114 is that more contact surface is engaged in a single thread rotation.

The insertion of the second section 114 into head of the metacarpal bone is followed by the insertion of the non-threaded section 116 of the stabilisation device. It is evident that the second section 116 of the stabilisation device 100 travels through a first section (head portion of the metacarpal bone) Progressing the second section 114 in the second section of the bore (within the body of the metacarpal bone) As the stabilisation device 100 is rotated further, the second section 114 of the stabilisation device progresses through the bore and enters a third section of the bore (base portion of the metacarpal bone) which in turn results in the non-threaded section 116 being located in the middle section of the bore (within the body of the metacarpal bone). Consequently, the first section 112 of the stabilisation device 100 becomes positioned within the first section of the bore in the bone (being stabilised). The first section 112 of the stabilisation device also includes a double thread structure which is beneficial for the same reasons as outlined in the previous sections. The pitch for the threads in the first section 112 is also substantially identical which ensures that the stabilisation device 100 does not apply a compressing force to bring any broken parts of the metacarpal bone M closer to each other by way of compression. The stabilisation device 100 has been shown in a stabilising configuration (stabilizing a typical metacarpal bone M) in FIG. 7. In other alternative embodiments, the pitch for the first section 112 may differ from the pitch of the second section 114. However, in such a scenario, the lead for the first section 112 and the second section 114 would need to be equal to achieve non-compressive stabilization as intended by the stabilization device 100. For example, in an alternative configuration, the first section 112 may have a single start thread whilst the second section 114 may have a double start thread. In such a scenario, in order for the lead on the second section 114 to be the same as the lead on the first section 112, the pitch for the second section 114 would need to be half of the pitch for the first section 112 in order to achieve non-compressive stabilization.

The progressively increasing diameter of the first section 112 from the first location 117 to the proximal end 120 of the stabilisation device 100 provides additional surface area along the outer wall of the first section 110 especially around the proximal end 120 and the head 122 of the stabilisation device 100 thereby engaging a greater volume of bone tissue in the head portion of the metacarpal bone M. The slightly enlarged configuration of the first section 112 particularly at the proximal end 120 of the stabilisation device 100 provides improved engagement with the head portion of the metacarpal bone M which has a greater volume relative to the body portion of the metacarpal bone M. Without being bound by theory, the applicants hypothesize that the enlarged head 122 of the stabilisation device 100 reduces the likelihood of the stabilisation device head 122 breaking during insertion of the device 100 into the metacarpal bone M.

Another important feature of the stabilisation device 100 in at least some embodiments relates to the non-threaded section 116. Once the stabilisation device 100 has been fully inserted into the metacarpal bone M, the non-threaded section 116 is located in the thinnest part (body) of the metacarpal bone M. Unlike conventional screws which include threads along the entire length of such screws, the absence of any threads along section 116 is very helpful. Typically, any load acting along a convention screw would be translated to the bone via threads cutting into the bone tissue. In a section of reduced bone volume, the provision of such threads cutting into such volume can lead to increased instances of bone damage in the body section of the metacarpal bone. The absence of any threads in section 116 reduces the likelihood of any additional stress or strain being applied on the body portion of the metacarpal bone M during use.

The following table provides exemplary lengths and diameters for the stabilisation device 100 manufactured in various different sizes to suit physiological requirements of various bone sizes.

| Diameter (D2/D3) | Length (L) | Increments for each length range | (L1) | (L2) | (L3) |
|---|---|---|---|---|---|
| 2.0 mm | 20-40 mm | 2 mm | 0.3 L | 0.3 L | 0.4 L |
| 2.5 mm | 30-60 mm | 5 mm | 0.3 L | 0.3 L | 0.4 L |
| 3.0 mm | 30-60 mm | 5 mm | 0.3 L | 0.3 L | 0.4 L |
| 3.0 mm | 70 mm | | 0.3 L | 0.3 L | 0.4 L |
| 3.5 mm | 40-60 mm | 5 mm | 0.3 L | 0.3 L | 0.4 L |
| 3.5 mm | 70 mm | | 0.3 L | 0.3 L | 0.4 L |
| 4.0 mm | 40-60 mm | 5 mm | 0.3 L | 0.3 L | 0.4 L |
| 4.0 mm | 70-80 mm | 10 mm | 0.3 L | 0.3 L | 0.4 L |
| 5.0 mm | 40-60 mm | 5 mm | 0.3 L | 0.3 L | 0.4 L |
| 5.0 mm | 70-90 mm | 10 mm | 0.3 L | 0.3 L | 0.4 L |

Figure 7:
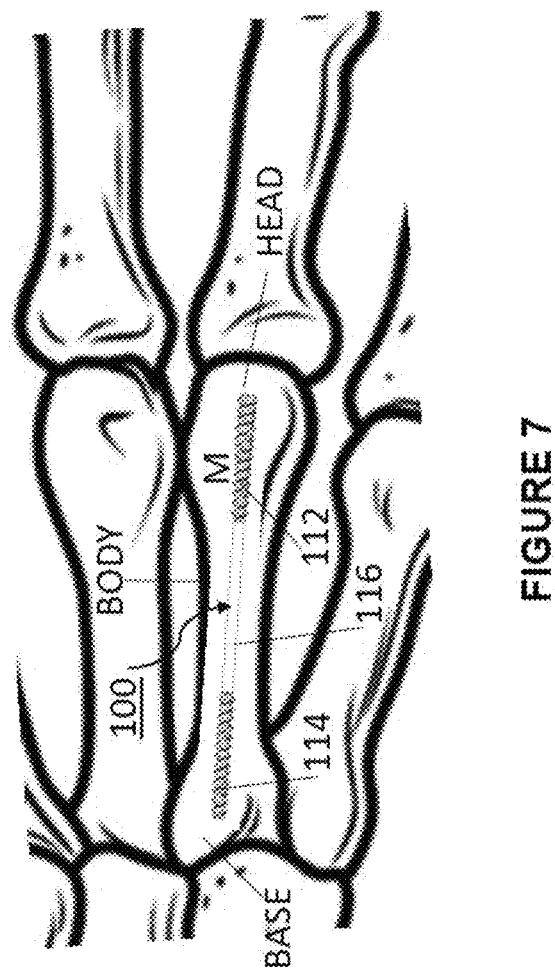
FIG. 7 is an in-use view of the bone stabilisation device 100 within a metacarpal bone M.
Figures 8, 9:
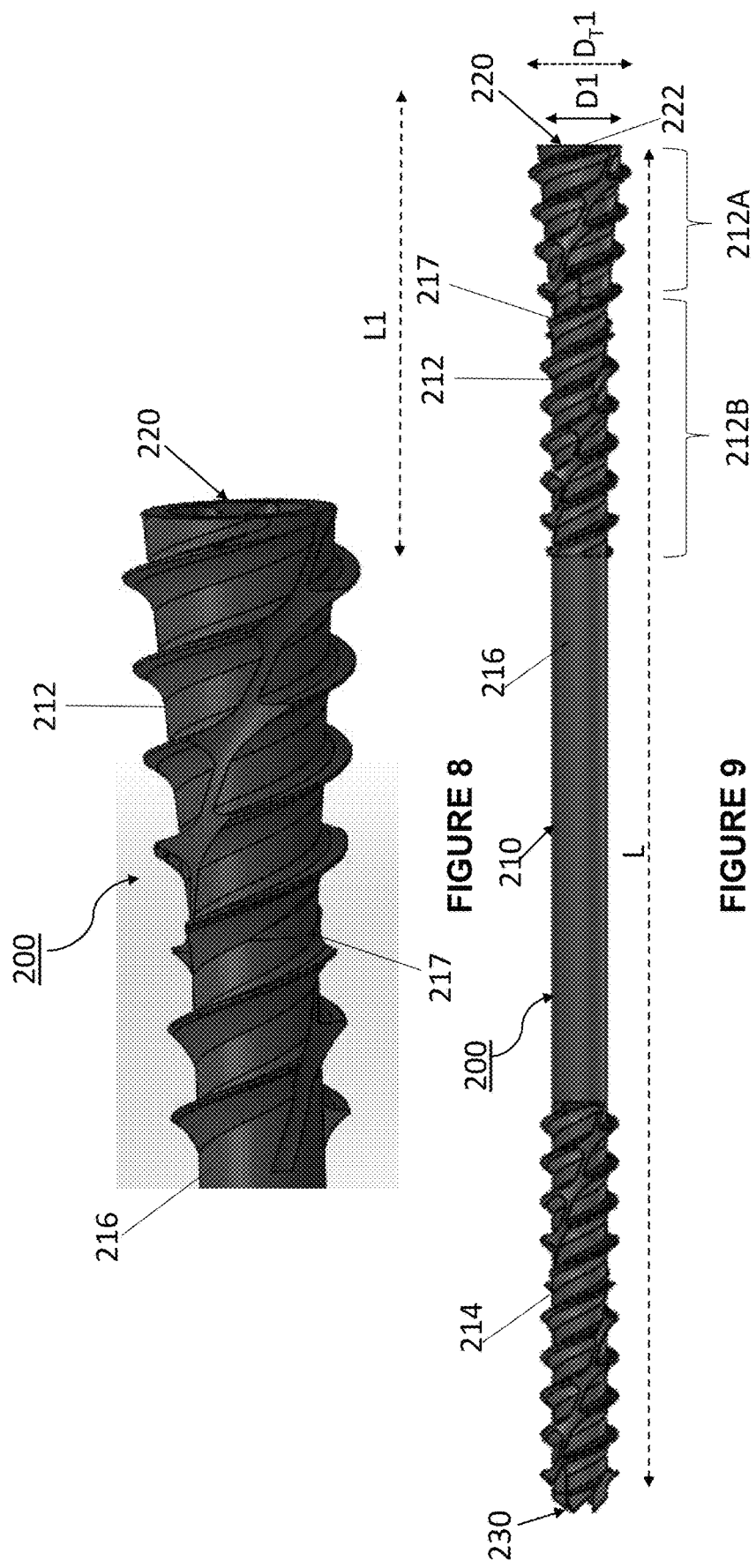
FIG. 8 is an enlarged view of the first section 212 of a bone stabilisation device 200 in accordance with a second embodiment.
FIG. 9 is a plan view of the bone stabilisation device 200.

Referring to FIGS. 8 and 9 a second embodiment of the stabilisation device 200 has been illustrated. The elongate body 210 of the device 200 comprises a first threaded section 212 and a second threaded section 214. The first threaded section 212 includes a head 222 located at the proximal end 220 that is adapted to interface with a driver. The head 222 may be configured to interface with any suitable driver configuration as explained in the earlier sections. The first threaded section 212 comprises a length (L1) whereby L1 is preferably 0.3 to 0.5 times the length (L) of the elongate body 110. Referring to FIG. 7 in particular, a first sub-section 212A of the first threaded section 212 extends from the proximal end 220 to a first location 217 of the elongate body 210 such that the outer thread diameter ($D_T1$) of the first sub section 212A gradually decreases from the proximal end 220 to the first location 217 along the first sub-section 212A. The outer thread diameter ($D_T1$) of the first section 212 along the second sub-section 212B is substantially constant.

In the preferred embodiment, the outer thread diameter ($D_T1$) decreases uniformly in a direction from the proximal end 220 towards the first location 217 to provide a substantially tapered configuration for the first sub-section 212A for the first threaded section 212. Preferably, the outer thread diameter ($D_T1$) of the first sub-section 212A at the proximal end 220 is 1.2 to 1.6 times the outer diameter ($D_T1$) of the first subs-section 212A at the first location 217 resulting in the initial tapered configuration of the first threaded sub-section 212A. The first threaded section 212 has a shank diameter denoted generally by D1. The shank diameter D1 of the first sub-section 212A also progressively decreases uniformly from the proximal end 220 towards the first location 217 and the shank diameter (D1) of the first sub-section at the proximal end is 1.2 to 1.6 times the shank diameter (D1) of the first sub-section 212A at the first location 217.

The configuration of the second section 214 in the device 200 is substantially similar to the configuration of the second section 114 as has been previously described in that the outer thread diameter and the shank diameter for the second section 214 remains substantially uniform along the length of the second section 214. The configuration of the non-threaded section 216 is also substantially similar to the non-threaded section 116 as previously described.

In compliance with the statute, the disclosure has been described in language more or less specific to structural or methodical features. The term "comprises" and its variations, such as "comprising" and "comprised of" is used throughout in an inclusive sense and not to the exclusion of any additional features.

It is to be understood that the disclosure is not limited to specific features shown or described since the means herein described comprises preferred forms of putting the disclosure into effect.

The disclosure is, therefore, claimed in any of its forms or modifications within the proper scope of the appended claims appropriately interpreted by those skilled in the art.

The invention claimed is:

1. An orthopaedic bone stabilization device comprising: an elongate and integrally formed body having a length (L) extending between a proximal end and a distal end, the elongate body further comprising:
   a first threaded section comprising a head located at the proximal end, the head being configured to interface with a driver, the first threaded section comprising external threads extending along a length (L1) of the first threaded section, the first threaded section extending between the proximal end of the elongate body and a first location of the elongate body wherein the first threaded section tapers from the proximal end to the first location such that outer thread diameter ($D_T1$) of the first threaded section gradually decreases from the proximal end to the first location of the elongate body wherein the first threaded section comprises one or more cutting flutes located at circumferentially spaced positions along the first threaded section and interrupting threads for the first threaded section, and:
   a second threaded section comprising external threads, the second threaded section having a length (L2) and a substantially uniform thread diameter ($D_T2$) and extending between the distal end of the elongate body and a second location of the elongate body;
   wherein the external threads on the first threaded section comprises a first lead and wherein the external threads on the second threaded section comprises a second lead such that the first lead is substantially similar to the second lead for providing non-compressive stabilization during use.

2. The orthopaedic bone stabilization device in accordance with claim 1 wherein the first and second threaded sections comprise the same number of starts for providing the non-compressive stabilization during use.

3. The orthopaedic bone stabilization device in accordance with claim 1 wherein the threads on the first section have the same pitch as the threads on the second section.

4. The orthopaedic bone stabilization device in accordance with claim 1 wherein the second threaded section comprises one or more cutting flutes and wherein the one or more cutting flutes are located at circumferentially spaced positioned along the second threaded sections and interrupting the threads.

5. The orthopaedic bone stabilization device in accordance with claim 1, further comprising a non-threaded section having a length (L3) positioned between the first and second threaded sections wherein said non-threaded section extends between the first and second locations of the elongate body.

6. The orthopaedic bone stabilization device in accordance with claim 5, wherein the non-threaded section comprises a uniform diameter along the length L3 of the non-threaded section.

7. The orthopaedic bone stabilization device in accordance with claim 5, wherein the length (L3) of the non-threaded section is less than 50% of the length of the elongate body.

8. The orthopaedic bone stabilization device in accordance with claim 5, wherein a shank diameter (D3) of the non-threaded section is substantially equal to a shank diameter (D2) of the second section.

9. The orthopaedic bone stabilization device in accordance with claim 1, wherein each of the first and second threaded sections comprises a respective shank diameter (D1 and D2 respectively).

10. The orthopaedic bone stabilization device in accordance with claim 1, wherein the outer thread diameter ($D_T1$) of the first section at the proximal end is 1.2 to 1.6 times the outer thread diameter ($D_T1$) of the first section at the first location.

11. The orthopaedic bone stabilization device in accordance with claim 1, wherein the outer thread diameter ($D_T1$) of the first section at the proximal end is 1.3 to 1.5 times the outer thread diameter ($D_T1$) of the first section at the first location.

12. The orthopaedic bone stabilization device in accordance with claim 1, wherein length (L1) of the first section is in the range of 0.2 L and 0.5 L.

13. The orthopaedic bone stabilization device in accordance with claim 1, wherein length (L1) of the first section is at least 0.25 L.

14. The orthopaedic bone stabilization device in accordance with claim 1, wherein length (L2) of the second section is in the range of 0.2 L and 0.5 L.

15. The orthopaedic bone stabilization device in accordance with claim 1, wherein length (L2) of the second section is at least 0.25 L.

16. The orthopaedic bone stabilization device in accordance with claim 1, wherein the elongate body comprises a cannulation extending through the length of the elongate body.

17. A method for repairing a bone utilizing an orthopaedic bone stabilization device, the device comprising: an elongate and integrally formed body having a length (L) extending between a proximal end and a distal end with a cannulation extending therethrough, the elongate body further comprising: a first threaded section comprising a head located at the proximal end, the head being configured to interface with a driver, the threaded section comprising external threads extending along a length (L1) of the first threaded section, the first threaded section extending between the proximal end of the elongate body and a first location of the elongate body wherein the first threaded section tapers from the proximal end to the first location such that outer thread diameter ($D_T1$) of the first section gradually decreases from the proximal end to the first location of the elongate body, and a second threaded section comprising external threads, the second threaded section having a length (L2) and a substantially uniform thread diameter ($D_T2$) and extending between the distal end of the elongate body and a second location of the elongate body wherein the external threads on the first threaded section comprises a first lead and wherein the external threads on the second threaded section comprises a second lead such that the first lead is substantially similar to the second lead, the method comprising including the steps of:
   (a) inserting a guide wire into a fractured bone to extend the guide wire across one or more fractures in the bone, and
   (b) positioning the entire length (L) of the bone stabilization device completely into the bone by (i) positioning the guide wire in the cannulation of the stabilization device, (ii) rotationally driving the device by engaging a driving end of a driving tool with the head of the device and rotatably driving the device using the driving tool over the guide wire until the device is positioned completely inside the opening on each side of the fracture in order to non-compressively stabilize the bone.

* * * * *